United States Patent
Ross et al.

(10) Patent No.: US 6,183,518 B1
(45) Date of Patent: Feb. 6, 2001

(54) METHOD OF REPLACING NUCLEUS PULPOSUS AND REPAIRING THE INTERVERTEBRAL DISK

(76) Inventors: Anthony C. Ross, 3546 Maybank Hwy., John's Island, SC (US) 29455; Peter A. Guagliano, 370 Bay Ridge Pkwy., Brooklyn, NY (US) 11209

(*) Notice: Under 35 U.S.C. 154(b), the term of this patent shall be extended for 0 days.

(21) Appl. No.: 09/274,217

(22) Filed: Mar. 23, 1999

Related U.S. Application Data

(63) Continuation-in-part of application No. 09/255,372, filed on Feb. 22, 1999.

(51) Int. Cl.[7] ............................... A61F 2/44; A61B 17/56
(52) U.S. Cl. ...................................... 623/17.16; 623/17.12
(58) Field of Search .................................. 623/17, 17.16, 623/17.12; 606/61

(56) References Cited

U.S. PATENT DOCUMENTS

| | | | |
|---|---|---|---|
| 5,047,055 | * | 9/1991 | Bae et al. ............................... 623/17 |
| 5,545,229 | * | 8/1996 | Parsons et al. ........................ 623/17 |
| 5,800,549 | * | 9/1998 | Bao et al. .............................. 623/17 |

* cited by examiner

*Primary Examiner*—Paul J. Hirsch
(74) *Attorney, Agent, or Firm*—Browning Bushman

(57) ABSTRACT

A process for repairing the annulus fibrosus, and replacing the nucleus pulposus. Removal of the nucleus pulposus and only as much of the annulus fibrosus and intervertebral disk as is necessary is performed. The tissue so removed is replaced by a material which is resilient, but non-dispersing upon setting. After application of the material, and after the material is set, the resiliency of the material permits motion of the vertebrae and performs the cushioning and joint functions of the intervertebral disk. The material is physiologically acceptable to the human body.

20 Claims, 2 Drawing Sheets

METHOD OF REPLACING NUCLEUS PULPOSUS AND REPAIRING THE INTERVERTEBRAL DISK

This application is a continuation-in-part of pending application Ser. No. 09/255,372, filed Feb. 22, 1999.

FIELD OF THE INVENTION

This invention relates to surgical methods generally, and is more specifically related to a process of repairing the intervertebral disk of mammals.

BACKGROUND OF THE INVENTION

Intervertebral disks are prone to injury. Due to the low blood supply to this area. intervertebral disks are slow to heal, and may not materially heal. When the annulus fibrosus is torn, or punctured, the nucleus pulposus can migrate. A ruptured/prolapsed annulus fibrosus is demonstrated in FIG. 1. A mechanical translation of the disk material is demonstrated in FIG. 2.

Annulus fibrosus, as referred to herein, is the marginal or peripheral portion of an intervertebral disk. The intervertebral disk is a disk with fibrous bands surrounding the nucleus pulposus occupying the space between two vertebra. The anatomy of the disk provides a cushion to allow motion, limit motion and provide space, distancing the vertebra off the nerves and compressible tissue. Part of the vertebrae are bony blocks, which, when stacked one upon the other, form the anterior portion of the spine. Annulus fibrosus is also known as annulus fibrosus disci intervertebralus. The nucleus pulposus is a substance of jelly like consistency found in the center of a intervertebral disk.

The effect of a ruptured/prolapsed annulus fibrosus may result in spasm, and neurological compromise, such as the compressed nerve indicated in FIG. 1 and other compressible soft tissues, i.e. arteries, veins. Degeneration of the condition may increase over time, resulting in chronic and debilitating pain. The condition is usually disabling.

Suppressive measures include steroidal injection, removal of the nucleus pulposus, and fusion either by donor bone, coral or by metal bracing. If disk removal is performed, a healthy part of the disk is often taken, eradicating the function of the joint, and accelerating the degeneration of adjacent segments of the body, as the body attempts to stabilize. This approach frequently leaves the patient immunologically and structurally compromised, if not permanently disabled.

Isolated treatment to only the damaged structures employing the most non-invasive procedure possible is preferred. This approach allows as much of the healthy tissue as possible to remain, and to retain normal neurological function. While the offending material can be removed, the material must be replaced with a material which will perform the function formerly performed by the material removed. A need exists for a process which limits the material removed from the intervertebral disk, and which replaces the material so removed with a composition that is physiologically acceptable to the human body, and which allows the intervertebral disk to retain motion and characteristics of normal joint function, including cushioning the joint as compression is introduce from the stacking of the vertebrae. The material must be pliable in its application, and non-dispersing after replacement.

SUMMARY OF THE PRESENT INVENTION

The present invention is a process of repairing the disk through replacing the nucleus pulposus. The process of the invention desires minimal invasiveness. Motion within the vertebrae, and joint function and cushioning in the intervertebral disk, are regained by the process.

The process involves removal of the nucleus pulposus and only as much of the annulus fibrosus and intervertebral disk as is necessary. The tissue so removed is replaced by a material which is resilient and non-dispersant upon setting, and within a temperature range of 35° and 42° C. After application of the material, and after the material is set, the resiliency of the material permits motion of the vertebrae, and performs the cushioning and joint functions of the intervertebral disk. The material is physiologically acceptable to the human body.

DETAILED DESCRIPTION OF THE PREFERRED EMBODIMENT

The rupture/prolapse of the annulus fibrosus is first identified and isolated. This identification and isolation is by means such as x-ray. MRI or other diagnostic imaging procedures which are diagnostically acceptable. After the area of rupture/prolapse is identified and isolated, the site is surgically accessed. Since it is a goal of the invention to minimize trauma associated with the procedure, it is preferred to access the site through an arthroscopic procedure, or technology that involves minimal invasion and offense to healthy areas of the annulus fibrosus, while damaged parts of the intervertebral disk are removed. Current technology allows for surgical removal of nucleus pulposus via irrigation and suction.

The material removed is replaced with a resilient material which physiologically acceptable to the human body. The material is first prepared so that it will have molten or semi-solid properties which allow transportation of the material to the site.

In the preferred embodiment, the material used for replacement of removed tissue is gutta percha, Gutta percha is a geometric isomer of natural rubber. A substance such as mineral trioxide aggregate may be added to the gutta percha to facilitate the binding properties, and to facilitate healing of the affected area.

Figure 1:
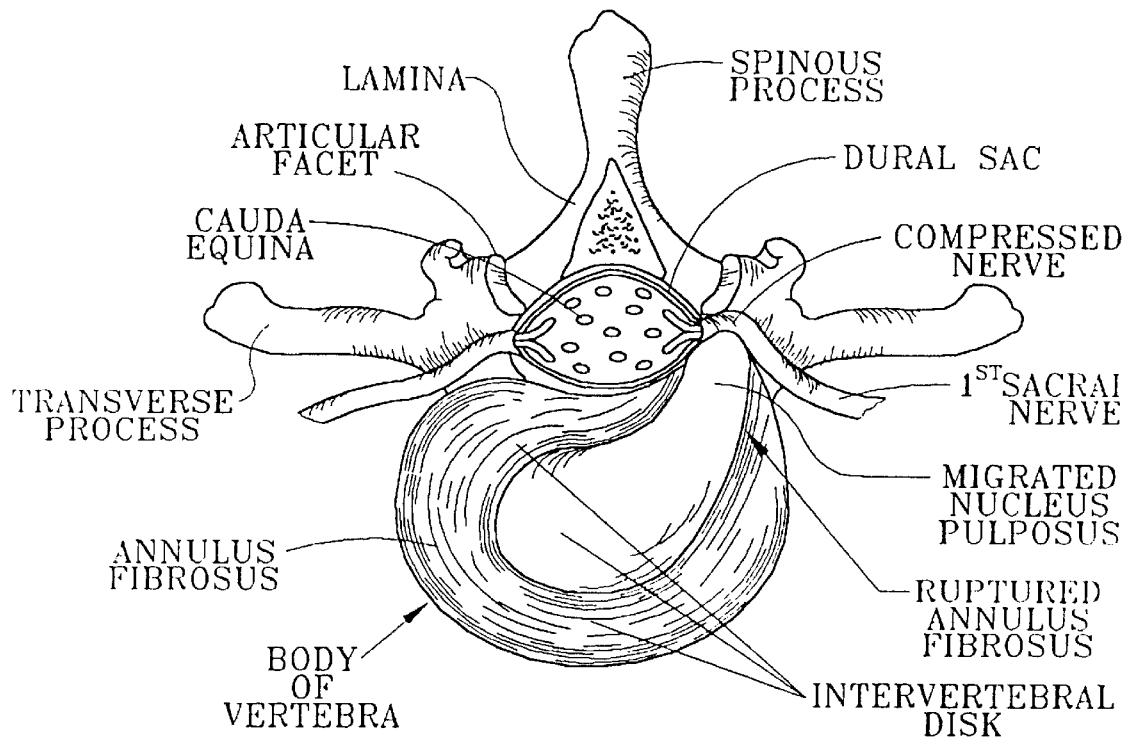
FIG. 1 shows, inter alia, a ruptured/prolapsed annulus fibrosus and the resulting migrated nucleus pulposus of an intervertebral disk.
Figure 2:
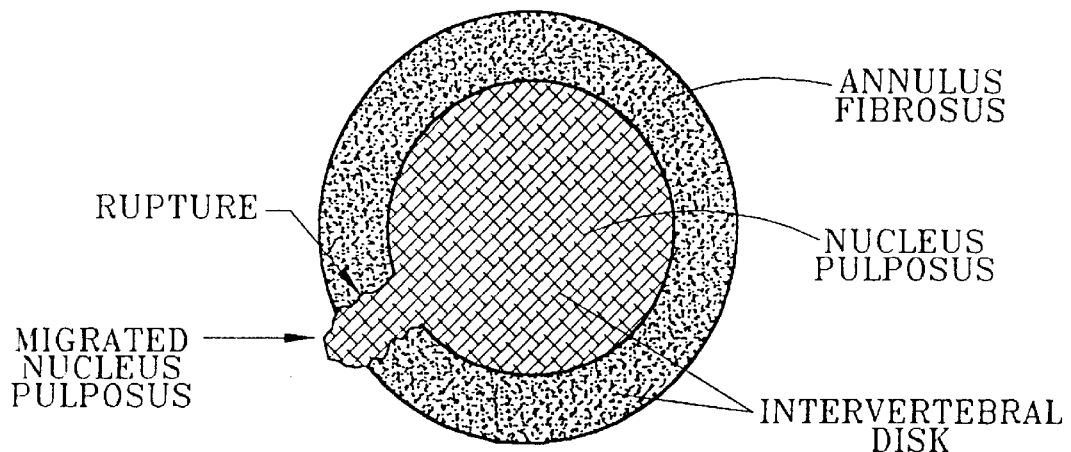
FIG. 2 demonstrates mechanical translation of a ruptured/prolapsed annulus fibrosus.
Figure 3:
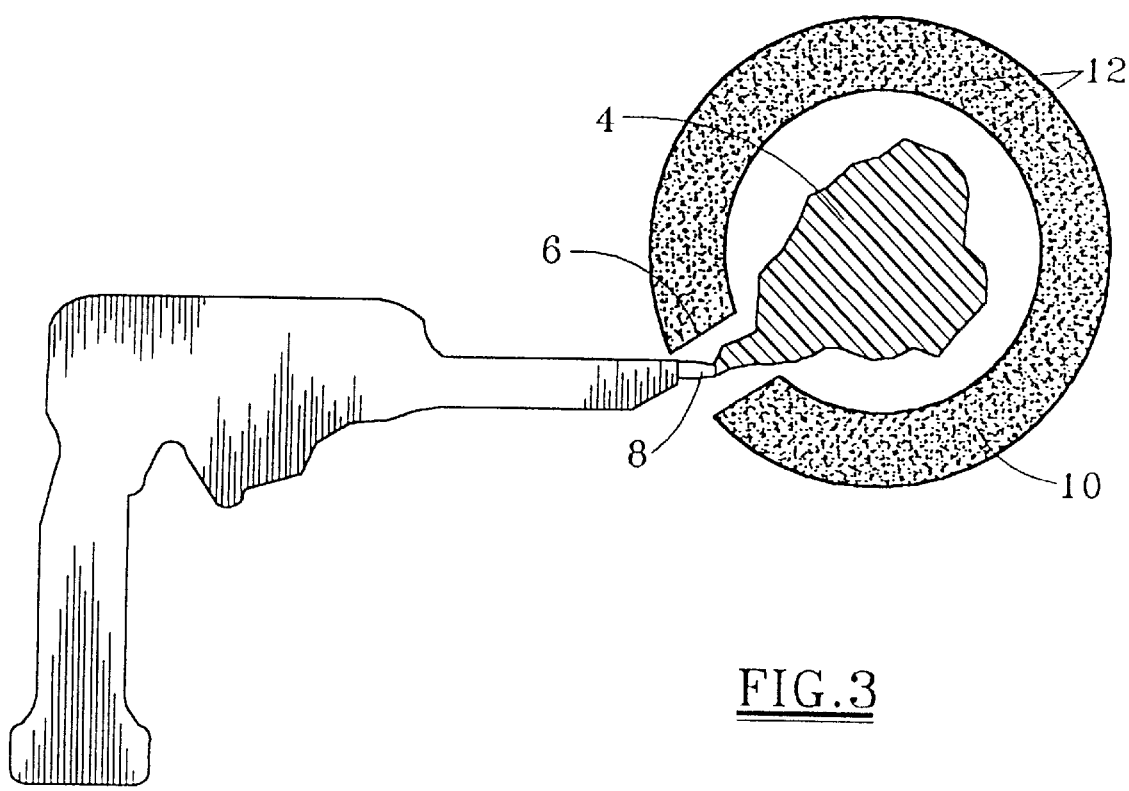
FIG. 3 demonstrates the replacement of the nucleus pulposus and the ruptured/prolapsed portion of the annulus fibrosus by the introduction of gutta percha via a mechanically facilitating device.
Figure 4:
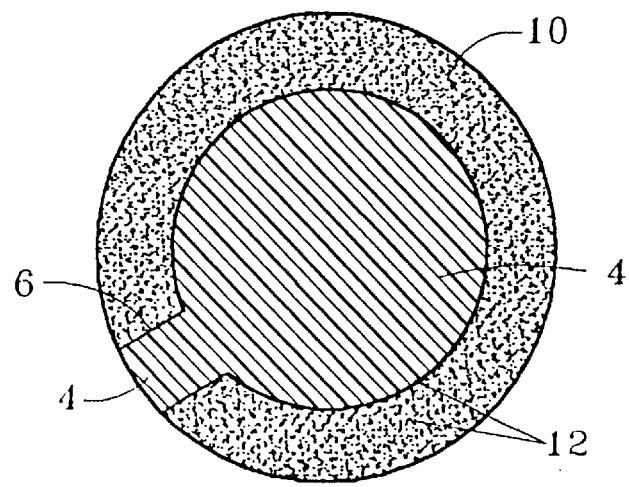
FIG. 4 demonstrates the intervertebral disk after repair with gutta percha.

When cold, gutta percha is relatively inelastic, but as it warms, it becomes moldable. At a high temperature, gutta percha will melt sufficiently to allow transportation of the material. Accordingly, the gutta percha is prepared by heating it to a sufficient temperature to melt the gutta percha. The gutta percha is then injected via mechanically facilitated means into the site. FIG. 3. replacing the tissue which has been surgically removed. The gutta percha may be transported into the site by means of an applicator 2 which applies pressure and directs the material through a nozzle 8 which may utilize insulated properties of ceramics. Dental gutta percha is reported to contain approximately 19–22% gutta percha, 1–4% plasticizing waxes and resins, 59–75% zinc oxide, 1–17% metal sulfates for radiopacity and trace amounts of organic dyes for coloration.

The applicator is designed to maintain the temperature of the gutta percha above ambient temperature so that the gutta percha flows, while also providing pressure control, which allows the gutta percha to be directed, and the flow volume and pressure controlled.

The gutta percha 4 replaces the nucleus pulposus and the affected area 6 of the annulus fibrosus 10, and, as applicable, the intervertebral disk 12. The volume of the removed tissue is replaced. Tractioning of the joint to create a negative (relative to ambient) pressure, to facilitate spacing and flow, may be employed.

As the gutta percha cools, the gutta percha will set. At normal human body temperatures, the gutta percha is no longer moldable, and it is not migratory. Accordingly, the gutta percha will remain in the site, filling the area formerly occupied by the nucleus pulposus, and repairing the rupture/prolapsed annulus fibrosus and associated migrated nucleus pulposus. The gutta percha is sufficiently resilient to restore the partial function previously performed by the intervertebral disk of cushioning a joint between the associated vertebrae.

If necessary, gutta percha may be subsequently removed from the site via surgical, physical, enzymatic and/or chemical means.

What is claimed is:

1. A process of replacing nucleus pulposus of an intervertebral disk, comprising the steps of:
   a. identifying a location of a prolapse in an annulus fibrosus of an intervertebral disk;
   b. removing nucleus pulposus associated with the said annulus fibrosus of said intervertebral disk;
   c. heating a resilient material which will not disperse upon setting; and
   d. pressurizing the heated resilient material and injecting the pressurized heated material through a thermally insulating nozzle into the intervertebral disk, such that the injected resilient material, upon setting, will occupy a space formerly occupied by said nucleus pulposus.

2. The process of replacing nucleus pulposus of an intervertebral disk as described in claim 1, further comprising:
   removing nucleus pulposus prior to injection of said heated resilient material, wherein said resilient material occupies a space formerly occupied by said nucleus pulposus.

3. The process of replacing nucleus pulposus of an intervertebral disk as described in claim 2, wherein said resilient material is a geometric isomer of natural rubber.

4. The process of replacing nucleus pulposus of an intervertebral disk as described in claim 2, wherein said resilient material is a geometric isomer of natural rubber.

5. The process of replacing nucleus pulposus of an intervertebral disk as described in claim 1, wherein said resilient material is dental gutta percha.

6. The process of replacing nucleus pulposus of an intervertebral disk as described in claim 2, wherein said resilient material is dental gutta percha.

7. The process of replacing nucleus pulposus of an intervertebral disk as described in claim 1, wherein the resilient material comprises gutta percha and zinc oxide.

8. The process for replacing nucleus pulposus of an intervertebral disk as described in claim 7, wherein the resilient material comprises approximately 19 to 22% gutta percha and 59 to 75% zinc oxide.

9. The process for replacing nucleus pulposus of an intervertebral disk as described in claim 7, wherein the resilient material further comprises plasticizing waxes and resins.

10. The process of replacing nucleus pulposus of an intervertebral disk as described in claim 7, wherein the resilient material further comprises metal sulfates.

11. The process of replacing nucleus pulposus of an intervertebral disk as described in claim 1, wherein removal of nucleus pulposus comprises irrigation and suction.

12. The process of replacing nucleus pulposus of an intervertebral disk as described in claim 1, further comprising:
    identifying the location of the pulposus with diagnostic imaging procedures.

13. The process of replacing nucleus pulposus of an intervertebral disk as described in claim 1, wherein the resilient material is heated to a temperature such that the resilient material is moldable.

14. A process of replacing nucleus pulposus of an intervertebral disk, comprising the steps of:
    a. identifying a location of a prolapse in an annulus fibrosus of an intervertebral disk;
    b. removing nucleus pulposus associated with the said annulus fibrosus of said intervertebral disk;
    c. thereafter heating to a moldable temperature geometric isomer of natural rubber material which will not disperse upon setting; and
    d. pressurizing the heated material and injecting the pressurized heated material through a thermally insulating nozzle into the intervertebral disk, such that the injected resilient material, upon setting, will occupy a space formerly occupied by said nucleus pulposus.

15. The process of replacing nucleus pulposus of an intervertebral disk as described in claim 14, wherein said material is dental gutta percha.

16. The process of replacing nucleus pulposus of an intervertebral disk as described in claim 14, wherein the material comprises gutta percha and zinc oxide.

17. The process for replacing nucleus pulposus of an intervertebral disk as described in claim 16, wherein the resilient material comprises approximately 19 to 22% gutta percha and 59 to 75% zinc oxide.

18. The process for replacing nucleus Pulposus of an intervertebral disk as described in claim 16, wherein the resilient material further comprises plasticizing waxes and resins.

19. The process of replacing nucleus pulposus of an intervertebral disk as described in claim 14, wherein removal of nucleus pulposus comprises irrigation and suction.

20. The process of replacing nucleus pulposus of an intervebral disk as described in claim 14, further comprising:
    identifying the location of the pulposus with diagnostic imaging procedures.

* * * * *